United States Patent [19]
Bull

[11] Patent Number: 5,169,315
[45] Date of Patent: Dec. 8, 1992

[54] MATERIAL HOLDING APPARATUS WITH INTEGRATED FINGER MOUNT AND CAP

[76] Inventor: Charles L. Bull, Lake Rd. 54-22, Box 468, Osage Beach, Mo. 65065

[21] Appl. No.: 880,881

[22] Filed: May 8, 1992

Related U.S. Application Data

[63] Continuation-in-part of Ser. No. 600,585, Oct. 19, 1990, Pat. No. 5,112,227.

[51] Int. Cl.⁵ .................. A61B 19/02; A41D 19/00; A61C 3/00
[52] U.S. Cl. .................. 433/163; 224/217; 206/63.5; 433/49
[58] Field of Search ............ 433/25, 49, 77, 163; 206/63.5, 368; 224/217

[56] References Cited

U.S. PATENT DOCUMENTS

| | | | |
|---|---|---|---|
| 902,109 | 10/1908 | Powell | 433/49 |
| 1,458,436 | 6/1923 | Pameyer | 224/217 X |
| 1,955,175 | 4/1934 | Crowther | 206/63.5 X |
| 2,356,722 | 8/1944 | Harris | 224/217 X |
| 2,539,940 | 1/1951 | Abramson | 224/217 |
| 2,665,479 | 1/1954 | Weldon | 433/163 |
| 3,327,391 | 6/1967 | Malm | 433/163 |
| 4,717,057 | 1/1988 | Porteous | 433/49 X |
| 4,844,308 | 7/1989 | Porteous | 224/217 |
| 4,901,847 | 2/1990 | Kesling | 433/49 X |

*Primary Examiner*—John J. Wilson
*Assistant Examiner*—Nicholas D. Lucchesi
*Attorney, Agent, or Firm*—Edward R. Weber

[57] ABSTRACT

A materials holding apparatus consisting of a receptacle, flange, and mount for use in the practice of dentistry capable of bringing the necessary implements to the operation at hand and making the requisite materials available for timely use, which can be worn on the finger or thumb of both left-handed and right-handed individuals with equal ease and remains stable and does not slip and slide around the finger or thumb. A protective cap is used in conjunction with the finger mounted apparatus to reduce spilling or splattering of the materials contained in the receptacle.

33 Claims, 2 Drawing Sheets

MATERIAL HOLDING APPARATUS WITH INTEGRATED FINGER MOUNT AND CAP

The present application is a continuation-in-part application under 35 U.S.C. §120 of prior application Ser. No. 07/600,585, filed Oct. 19, 1990, now U.S. Pat. No. 5,112,227.

FIELD OF THE INVENTION

The present invention relates to material holding apparatus and more particularly, to finger mounted cups and trays used in conjunction with materials used in the practice of dentistry, and to protective caps used in conjunction with the finger mounted cups or trays to reduce spilling or splattering of material contained in the cup.

BACKGROUND OF THE INVENTION

In working with patients, dental professionals are faced with the need to keep instruments, materials and patients in a compact area to reduce the time and inconvenience associated with bringing the necessary implements to the operation at hand and making the requisite materials available for timely use. As a result, a multitude of chairs, tables, instruments and dental accessories have been developed to address these needs. Material handling cups and trays, both with slip-fitted or snap-connected finger mounts and with integrated finger mounts, are but one of the dental accessories designed to meet both challenges.

The prior art has addressed these concerns in a number of fashions. U.S. Pat. No. 3,327,391 (Malm) shows a finger mounted holding apparatus with a snap fitted cup, which in one embodiment is disposable. The shortcoming of the device lies in the need for precision in the manufacturing of the mating mechanism of the cup and of the finger mount to ensure first, that the two parts will mate and second, that the mated apparatus will be stable during use by the dental professional.

U.S. Pat. No. 902,109 (Powell) shows a finger mounted tray. As will be understood, the shortcoming of this apparatus lies in its inability to handle materials in liquid form. It also is not disposable and thus requires cleaning and sterilizing.

U.S. Pat. No. 2,222,741 (Bush) shows a cup which is slidably attached to a finger ring and is held in the palm of the hand during use. The ends of the finger ring, which is constructed of lightweight metal, overlap so that the ring can be inserted through a bore on the cup and closed by clamping the ring to fit the finger. It will be understood that the constant opening of the ring for mating with the cup and clamping of the ring to fit the finger of the particular dental professional using the device will cause the ring to fail.

Unfortunately, as extensive as the prior art is, shortcomings associated with the use of material handling apparatus still exist and improvements can still be made. One such problem is that repeated use of material handling apparatus which incorporate slip-fitted finger mounts causes the device to slip and slide about the finger when an instrument is dipped into the contents of the cup. A similar problem is that repeated use of snap-fitted finger mounts wears the mating surface resulting in an unstable device. Another consideration is the desirability of free movement of the dental professional's hand during the operation. Additionally, material handling apparatus must be manufactured from materials that are chemically stable when used with various prophylactic remedies, filling materials, medications and other substances used in connection with the practice of dentistry.

Accordingly it is the primary object of the present invention to provide a finger mounted material handling apparatus that remains stable and does not slip and slide around the finger. It is a further object of the present invention to provide a material handling apparatus which will not interfere with or obstruct free use of the dental professional's hand. It is another object of the present invention to provide a lightweight device consisting of an integrated cup and finger mount which is simple in construction, economical to manufacture, and efficient in use. Still another object of the invention is to provide a cap to mate with the integrated cup so as to aid in avoiding unwanted spillage or spattering of the material in the cup when an instrument is used to withdraw a desired portion of the material. Other objects and features will be in part apparent and in part pointed out hereinafter.

SUMMARY OF THE INVENTION

The present invention is intended to be worn on a finger or thumb of a dental professional when handling prophylactic remedies, in particular, but also filling materials, medications or other substances used in the practice of dentistry. It is simple in construction being a unitary material holding piece consisting of a cup, a platform defining a flange, a split finger ring, and a mating cap having an opening with a reentrant lip. The device can be constructed of any of numerous known materials which are capable of holding substances associated with the practice of dentistry without chemically interacting therewith, such as thermosetting materials and thermoplastic materials, including polyethylene and polypropylene and copolymers of polyethylene and polypropylene. In a preferred embodiment, the device would be of a polyethylene resin, or other suitable plastic, which would be injection molded.

As stated earlier, one element of the device is a unitary material holding piece. The cup portion of the material holding piece, which has an open mouth defined by a rim, converges perpendicularly with an elliptical platform which defines the bottom of the cup portion, forms a flange projecting from the bottom of the cup, acts as a stabilizer when worn on the finger or thumb, and, to a certain degree, protects the finger or thumb of the dental professional from dribbled substances. Opposite the cup portion, the elliptical platform converges with a finger ring which terminates in a pair of inwardly arcuate members, the ends of which are spaced. The finger ring is of such dimension as to be flexible for use on the finger or thumb of a wide variety of individuals.

In use, the device is slipped over whatever finger or thumb the dental professional finds suitable for his particular style of practice. As will be appreciated, the device could be worn in a plane parallel to that of the hand. It likewise could be worn in a plane perpendicular to that of the hand. Thus, the hand of the dental professional will be free to move in any manner the professional requires. As will be further appreciated, the platform surrounding the cup portion will maintain the device in an upright position and prevent the device from sliding around the finger or thumb. Additionally, inasmuch as the cup is substantially centered on the platform, the device is symmetrical and can be used by both left-handed and right-handed individuals with equal ease.

The device is further provided with a cap element which mates with the cup portion to produce a reentrant lip. The reentrant lip projects inwardly and reduces splashing and splattering when a dental instrument is inserted in the material in the cup and reduces the tendency of the material to spill when the hand is tilted.

In a preferred embodiment, the device is inexpensively constructed of materials, such as polyethylene resin, to allow the device to be used once and thereafter disposed of. It also is provided to dental professionals with prophylactic paste enclosed in the cup portion, the cup being sealed with film suitable for such purposes, manufactured from materials commonly used for hygienic seals, via adhesive or heat activated means. However, it should be understood that either or both elements of the device could also be manufactured so that they could be cleaned and sterilized for re-use. The device likewise could hold substances other than prophylactic remedies.

It should also be appreciated that the material holding apparatus of the present invention is not limited to use by the dental profession. It could similarly be employed by artisans using paints, attaching beads, or engaging in various other endeavors, by individuals working with small parts, by jewelers utilizing etching solutions, among others.

DETAILED DESCRIPTION OF THE DRAWINGS

Figure 1:
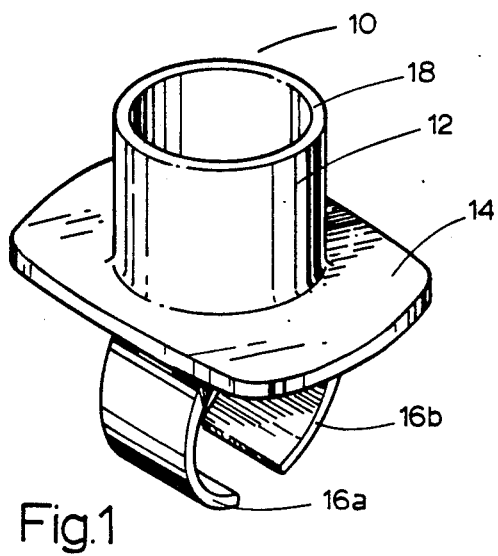
FIG. 1 is a diagrammatic view of an embodiment of the material holding element of the present invention showing the cup portion, platform and split finger ring.

Referring now to the drawings wherein like reference characters represent like elements, FIGS. 1 through 10 illustrate one embodiment of the device of the present invention.

In FIG. 1, material holding element 10 consists of three primary substructures: a cup 12, a platform 14 and a split finger ring 16. Cup 12 has an open mouth defined by a rim 18 and converges perpendicularly with platform 14, which defines the bottom of cup 12. Cup 12 is substantially centered on platform 14 and is constructed to have a dimension suitable for holding one application of a prophylactic remedy or other material, medication or substance used in the practice of dentistry.

Platform 14 is elliptical in shape and of a width correlative to that of a finger or thumb to prevent element 10 from sliding around finger 20 or thumb 22. The length of platform 14 is similarly correlative to the length of a finger or thumb segment to further stabilize element 10 when in use. This can be better seen in FIGS. 3 and 4.

Figure 2:
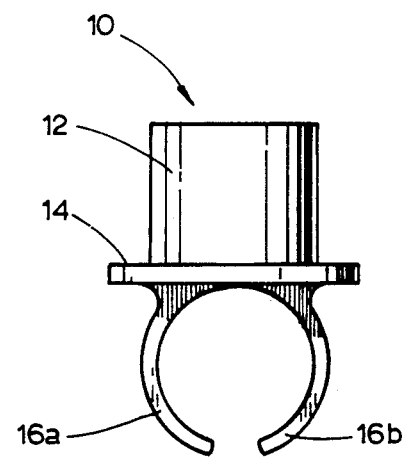
FIG. 2 is a side elevational view of an embodiment of the present invention.
Figure 3:
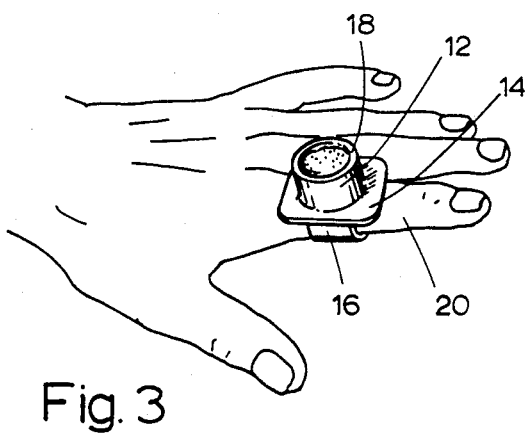
FIG. 3 is an elevational view of an embodiment of the present invention shown worn on a finger in the plane of the hand.
Figure 4:
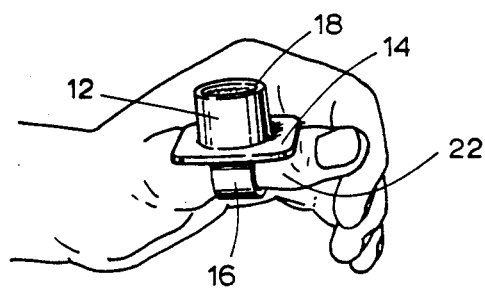
FIG. 4 is an elevational view of an embodiment of the present invention shown worn on the thumb in a plane perpendicular to that of the hand.

Opposite cup 12, platform 14 converges with split finger ring 16 which consists of two subparts 16a and 16b. Subparts 16a and 16b, which can best be seen in FIG. 2, are inwardly arcuate members which terminate in spaced relation to each other.

Figure 5:
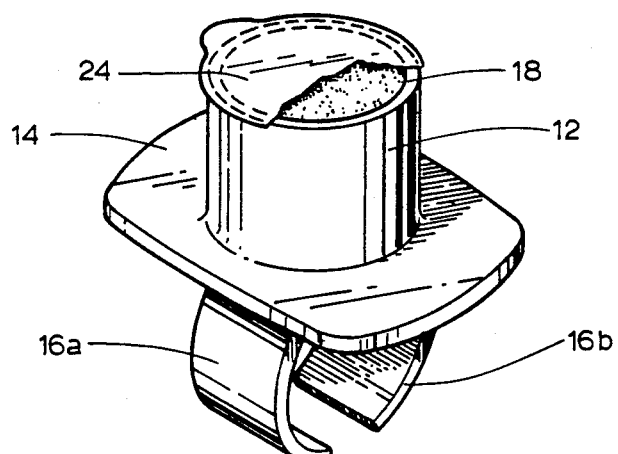
FIG. 5 is an elevational plan view of an embodiment of the present invention showing a closure in fragmentary section.

FIG. 5 demonstrates an embodiment in which a closure 24 is provided which affixes to rim 18 of cup 12 to enclose and seal the contents of cup 12.

Figure 6:
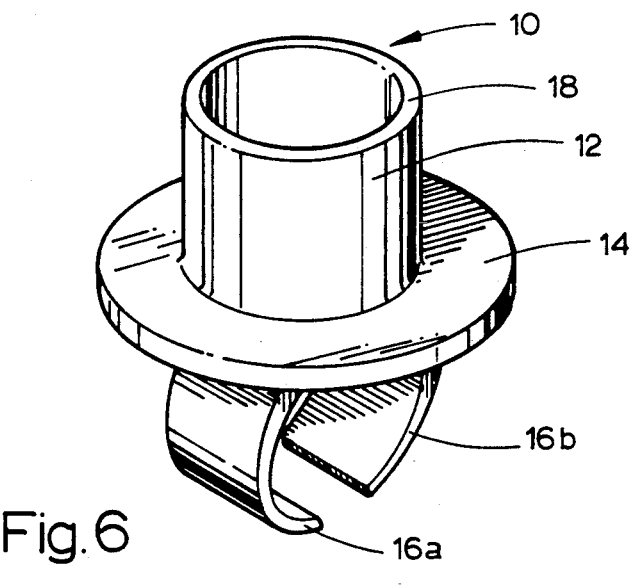
FIG. 6 is a diagrammatic view of an additional embodiment of the present invention wherein the platform is circular.
Figure 7:
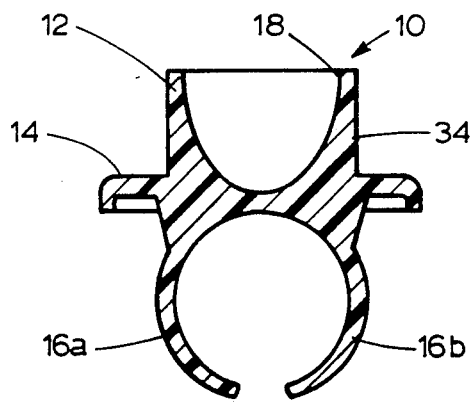
FIG. 7 is a cross-sectional view of a side elevation of an embodiment of the material holding element of the present invention.

In FIG. 6, an additional embodiment of the material holding element 10 shows platform 14 as circular in shape and of a width correlative to that of a finger or thumb to prevent element 10 from sliding around the digit.

Figure 8:
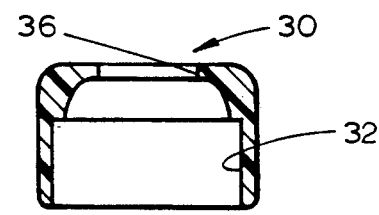
FIG. 8 is a cross-sectional view of a side elevation of the cap element of the present invention.
Figure 9:
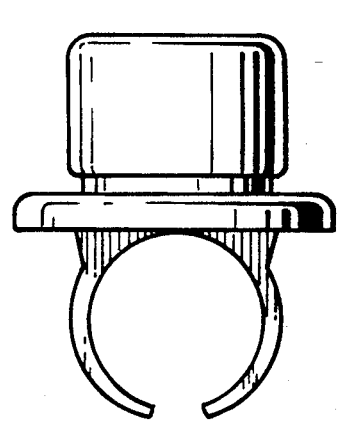
FIG. 9 is a side elevation of the material holding element of the present invention in mating relationship with the cap element.
Figure 10:
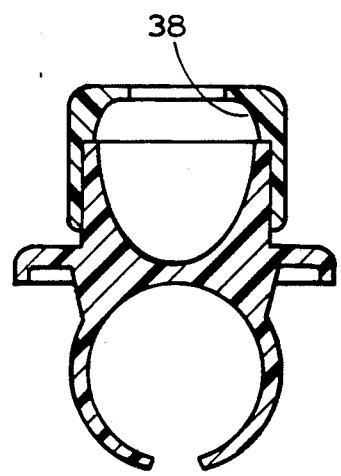
FIG. 10 is a cross-sectional view of the mated elements of FIG. 9 which illustrates the reentrant lip of the cap element.

FIG. 8 illustrates a cap structure 30 which mates with cup 12 to form an assembly which provides improved anti-spill and anti-splatter characteristics. Cap 30 is a unitary structure sized to removably engage cup 12. Its radial shape is identical to the radial shape of cup 12. Interior wall 32 is fabricated to surround exterior wall 34 of cup 12 and to engage exterior wall 34 in a snug slip fit. This is shown in FIGS. 9 and 10. Cap 30 further has a reduced diameter opening 36 such that when cap 30 is mated with cup 12, a reentrant lip offers multiple benefits, including providing a means for the user of the contents of the cup to control the amount of material removed by the tool used for treatment and reducing any tendency of the material in the cup to spill from the cup.

From the foregoing description, it will be readily understood that the material handling apparatus can be placed by a dental professional on any finger or thumb which meets his particular style of practice. When the apparatus is in place, the platform maintains placement thereof by reducing the amount of movement possible. As will be appreciated, the apparatus will remain stable even when a dental instrument is dipped into the contents of the cup. Furthermore, any excess material on the dental instrument may be scraped from the instrument on the reentrant lip and contained in the cup for future use. Additionally, the stability provided by the platform when coupled with the choice of placement of the apparatus by the dental professional will prevent interference with or obstruction to the free use of the hand. In a preferred embodiment, the unitary construction is lightweight and simple and economical to manufacture. Lastly, it will be recognized that the apparatus will be extremely efficient during use if it comes with prepackaged remedies, medications, or other substances and is disposable.

As suggested above, it will be understood that the material handling apparatus of the present invention could be manufactured to be either a disposable or non-disposable product. Likewise, contents of various types could be sealed within the product or not. Additionally, the cup could have a variety of shapes consistent with the type and amount of materials sealed within. Similarly, the flange could be round in shape. As various other changes could be made in the above product without departing from the spirit and scope of the invention, it is intended that all matter contained in the above description or shown in the accompanying drawings shall be interpreted as illustrative and not in a limiting sense.

In view of the above, it will be seen that the several objects of the invention are achieved and other advantageous results attained.

What is claimed is:

1. A device for holding materials sized to fit the human hand consisting of a receptacle, a platform creating a planar flange, and a means adapted to mount said device on a finger of a user wherein said receptacle consists of a generally cylindrical wall having an open mouth at a first end and converging perpendicularly at its second end with a first side of said platform, a portion of said first side of said platform creating the bottom of said receptacle; and wherein said platform provides stability to said device when said device is in use; and wherein said means consists of a band adapted to be adjustable to fit a variety of finger sizes, said means extending from a second side of said platform at a location opposite the area where said receptacle converges with said platform; and wherein said band is adapted to detachably position said device on the finger of the user; and wherein said receptacle, said platform, and said means adapted to mount said device on a finger of a user are all part of a single unitary device formed from a single piece of material and wherein said receptacle is in the center of said platform and is substantially concentric therewith; and further wherein a means is provided for reducing the size of the open mouth of said receptacle to create a reentrant lip.

2. A device for holding materials according to claim 1 wherein said means adapted to mount said device on a finger of a user consists of two inwardly arcuate members projecting from said second side of said platform, which arcuate members individually terminate at separate locations adjacent each other and spaced away from said platform.

3. A device for holding materials according to claim 1 wherein said receptacle, said platform, and said means adapted to mount said device on a finger are integrally formed from one piece of material.

4. A device for holding materials according to claim 3 wherein said receptacle, said platform, and said band are integrally formed by molding.

5. A device for holding materials according to claim 3 wherein said receptacle, said platform, and said means adapted to mount said device on a finger are integrally formed form one piece of thermosetting material.

6. A device for holding materials according to claim 3 wherein said receptacle, said platform, and said means adapted to mount said device on a finger are integrally formed form one piece of thermoplastic material.

7. A device for holding materials according to claim 1 wherein said means for creating a reentrant lip consists of a cap formed from one piece of material.

8. A device for holding materials according to claim 7 wherein said cap is formed by molding.

9. A device for holding materials according to claim 1 wherein said receptacle is a cylinder open at one end and said reentrant lip is produced by a cap with an opening smaller than the size of the open end of said cylinder which is mated with said open end of said cylinder.

10. A device for holding materials according to claim 1 wherein said platform is an ellipsoid.

11. A device for holding materials according to claim 1 wherein said platform is circular.

12. A device for holding materials according to claim 1 wherein said open mouth of said receptacle is sealed by a closure which is impervious to liquids and gases, which closure serves to retain a predetermined quantity of the desired material in said receptacle.

13. A materials holding device according to claim 12 wherein said closure is affixed to said receptacle via adhesive means.

14. A materials holding device according to claim 12 wherein said closure is affixed to said receptacle via heat activated means.

15. A materials holding device according to claim 12 wherein said closure is manufactured from materials commonly used for hygienic seals.

16. A device for holding materials according to claim 1 manufactured from the family of thermoplastic materials which includes polyethylene and polypropylene and co-polymers of polyethylene and polypropylene.

17. A materials holding device sized to fit the human hand consisting of a receptacle, a platform creating a planar flange, and a positioning means all formed from a single piece of material wherein said receptacle consists of a generally cylindrical wall having an open mouth defined by the interior rim of said wall and a means of reducing the size of said open mouth to produce a reentrant lip at a first end and the exterior of said generally cylindrical wall converging substantially perpendicularly at its second end with a first side of said platform, a portion of said first side of said platform creating the bottom of said receptacle; and wherein said platform stabilizes said device on the hand of said user when said device is in use; and wherein said positioning means extends from a second side of said platform at a location opposite the area where said receptacle converges with said platform; and wherein said positioning means is adapted to detachably position said device on the hand of the user and wherein said receptacle is in the center of said platform and is substantially concentric therewith.

18. A materials holding device according to claim 17 wherein said receptacle, said platform, and said positioning means are integrally formed from one piece of material and wherein said reentrant lip is created by a separate cap suitably sized to mate with the exterior of said receptacle.

19. A materials holding device according to claim 18 wherein said receptacle, said platform, and said positioning means are integrally formed by molding.

20. A materials holding device according to claim 18 wherein said cap is formed by molding.

21. A materials holding device according to claim 18 wherein said receptacle, said platform, and said positioning means are integrally formed from one piece of thermosetting material.

22. A materials holding device according to claim 18 wherein said cap is formed from one piece of thermosetting material.

23. A materials holding device according to claim 18 wherein said receptacle, said platform, and said positioning means are integrally formed from one piece of thermoplastic material.

24. A materials holding device according to claim 18 wherein said cap is formed from one piece of thermoplastic material.

25. A materials holding device according to claim 17 wherein said receptacle is a cylinder open at one end and said reentrant lip is produced by a cap with an opening smaller than the size of the open end of said cylinder which is mated with said open end of said cylinder.

26. A materials holding device according to claim 17 wherein said platform is an ellipsoid.

27. A materials holding device according to claim 17 wherein said platform is circular.

28. A materials holding device according to claim 17 wherein said positioning means consists of two inwardly arcuate members which terminate in spaced relation.

29. A materials holding device according to claim 17 wherein said open mouth of said receptacle is sealed at its rim by a closure which is impervious to liquids and gases, which closure serves to retain a predetermined quantity of a desired material in said receptacle.

30. A materials holding device according to claim 29 wherein said closure is affixed to said rim of said receptacle via adhesive means.

31. A materials holding device according to claim 29 wherein said closure is affixed to said rim of said receptacle via heat activated means.

32. A materials holding device according to claim 29 wherein said closure is manufactured from materials commonly used for hygienic seals.

33. A materials holding device according to claim 17 manufactured from the family of thermoplastic materials which includes polyethylene and polypropylene and co-polymers of polyethylene and polypropylene.

* * * * *